(12) United States Patent
Sakuma (10) Patent No.: US 10,413,489 B2
(45) Date of Patent: Sep. 17, 2019

(54) COSMETIC COMPOSITION (71) Applicant: MITSUBISHI PENCIL COMPANY, LIMITED, Shinagawa-ku (JP)

(72) Inventor: Satoshi Sakuma, Fujioka (JP)

(73) Assignee: MITSUBISHI PENCIL COMPANY, LIMITED, Shinagawa-Ku, Toyko (JP)

( * ) Notice: Subject to any disclaimer, the term of this patent is extended or adjusted under 35 U.S.C. 154(b) by 83 days.

(21) Appl. No.: 14/602,506

(22) Filed: Jan. 22, 2015

(65) Prior Publication Data
US 2015/0216771 A1 Aug. 6, 2015

(30) Foreign Application Priority Data

Feb. 4, 2014 (JP) .................................. 2014-019307
Dec. 26, 2014 (JP) .................................. 2014-264613

(51) Int. Cl.
| | | |
|---|---|---|
| *A61K 8/02* | (2006.01) | |
| *A61K 8/04* | (2006.01) | |
| *A61K 8/19* | (2006.01) | |
| *A61K 8/88* | (2006.01) | |
| *A61Q 1/10* | (2006.01) | |
| *A61K 8/365* | (2006.01) | |

(52) U.S. Cl.
CPC .............. *A61K 8/19* (2013.01); *A61K 8/0241* (2013.01); *A61K 8/044* (2013.01); *A61K 8/365* (2013.01); *A61K 8/88* (2013.01); *A61Q 1/10* (2013.01); *A61K 2800/413* (2013.01); *A61K 2800/5424* (2013.01)

(58) Field of Classification Search
CPC ........ A61K 8/19; A61K 8/0241; A61K 8/044; A61K 8/365; A61K 8/88; A61K 2800/413; A61K 2800/5424; A61Q 1/10
See application file for complete search history.

(56) References Cited

U.S. PATENT DOCUMENTS

| | | | | |
|---|---|---|---|---|
| 5,013,543 A | * | 5/1991 | Mercado ............... | A61K 8/8176 424/63 |
| 5,534,247 A | | 7/1996 | Franjac et al. | |
| 9,168,208 B2 | | 10/2015 | Matsushita | |
| 2005/0002881 A1 | * | 1/2005 | Aota ..................... | A61K 8/044 424/63 |
| 2010/0221204 A1 | | 9/2010 | Morita et al. | |
| 2014/0017288 A1 | | 1/2014 | Matsushita | |

FOREIGN PATENT DOCUMENTS

| | | | | |
|---|---|---|---|---|
| FR | 2981846 A1 | * | 5/2013 | ............... A61K 8/24 |
| JP | S62-84017 A | | 4/1987 | |
| JP | 4-66447 B2 | | 10/1992 | |
| JP | 2003-231614 A | | 8/2003 | |
| JP | 2004-315459 A | | 11/2004 | |
| JP | 2005-187397 A | | 7/2005 | |
| JP | 2007-106714 A | | 4/2007 | |
| JP | 2012-001503 A | | 1/2012 | |
| JP | 2012-184181 A | | 9/2012 | |
| JP | 2014-101298 A | | 6/2014 | |
| WO | 2012/102296 A1 | | 8/2012 | |

OTHER PUBLICATIONS

Search Report issued by the French Patent Office in corresponding French Patent Application No. 1550753 dated May 4, 2018 (3 pages).

* cited by examiner

*Primary Examiner* — John Pak
*Assistant Examiner* — Nathan W Schlientz
(74) *Attorney, Agent, or Firm* — Buchanan, Ingersoll & Rooney PC (57) ABSTRACT

The cosmetic composition of the present invention is characterized by containing an anionic polymer dispersant, an acid having a molecular weight of 300 or less and iron oxide particles, wherein a viscosity of the cosmetic is 15 mPa·s or less, and an average particle diameter of the iron oxide particles in the cosmetic is 100 nm or less. The above cosmetic composition is excellent in an aging stability and can be used by charging in a liquid cosmetic applicator.

8 Claims, 3 Drawing Sheets

COSMETIC COMPOSITION

This nonprovisional application claims priority under 35 U.S.C. § 119(a) on Patent Application No. 2014-019307 filed in Japan on 4 Feb. 2014, the entire contents of which are hereby incorporated by reference.

BACKGROUND OF THE INVENTION (1) Field of the Invention

The present invention relates to a cosmetic composition, more specifically to a cosmetic composition which is prepared by using iron oxide particles of red iron oxide and the like as a coloring material for liquid cosmetics and which is suitable for eyeliners and excellent in a dispersibility and an aging stability.

(2) Description of Related Art

From the past up to the present time, coloring materials for cosmetics have so far been restricted in use from the viewpoint of a safety. In particular, coloring materials which can be used for cosmetics for eye makeup such as eyeliners are restricted. In general, coloring materials are classified into dyes and pigments, and coloring matters are deposited in a case of the dyes, so that the pigments are being increased recently in use. Among them, inorganic pigments which can be used at ease in terms of a safety are usually used.

However, the inorganic pigments have involved the problem that in a case of, for example, iron oxide, it has a high specific gravity and a large primary particle diameter and that it settles down for short time in a low viscous composition to cause color separation.

Known as patent documents in which iron oxide is used as a pigment for liquid cosmetics are, for example, 1) eye makeup cosmetics comprising aqueous dispersions which contain (A) an iron base inorganic pigment, (B) an anionic polymer compound and (C) at least one chelating agent selected from ethylenediaminehyroxyethyl triacetate and salts thereof and which have a viscosity of 3 to 300 cps (centipoise) at a temperature of 25° C. (refer to, for example, Japanese Patent Publication No. 1992-66447), 2) pigment dispersions for cosmetics containing black iron oxide, red iron oxide and Prussian blue, and eyeliners prepared by charging a pen type vessel with the above dispersion (refer to, for example, Japanese Patent Application Laid-Open No. 2003-23614), 3) pigment dispersions for cosmetics containing poly-γ-L-glutamic acid and/or salts thereof, black iron oxide, red iron oxide and Prussian blue, and eyeliners prepared by charging a pen type vessel with the above dispersion (refer to, for example, Japanese Patent Application Laid-Open No. 2012-1503), and 4) pigment dispersions for cosmetics prepared by using black iron oxide in combination with a small amount of red iron oxide and blending additionally α-olefin sulfonic acid salt, and eyeliners prepared by charging a pen type vessel with the above dispersion (refer to, for example, Japanese Patent Application Laid-Open No. 2012-184181).

However, in the compositions for cosmetics described in the patent documents described above, whereas the effects can be exerted in a part of the pen type specifications thereof, the bulk substances settle down and are separated, and therefore involved therein is the problem that when the pen type structure is changed, it is difficult to exert the effects thereof.

In general, brown color base compositions for eyeliners are toned by adding carbon black to red iron oxide, but the existing situation is that because of a high specific gravity and a large particle diameter of red iron oxide, problems such as color separation and the like are involved therein.

SUMMARY OF THE INVENTION

In light of the problems on the conventional techniques and the existing situation each described above, the present invention intends to solve them, and an object thereof is to provide a cosmetic composition which does not bring about precipitation and color separation even when iron oxide particles of red iron oxide and the like are used as a coloring material for a liquid cosmetic and which is excellent in a dispersibility and an aging stability.

In light of the conventional problems described above and the like, intense researches repeated by the present inventors have resulted in finding that a cosmetic composition meeting the object described above is obtained by a composition containing a specific polymer dispersant, a specific acid and iron oxide particles, wherein a viscosity thereof is controlled to a specific value or lower, and an average particle diameter of the iron oxide particles in the cosmetic is controlled to a specific value or lower. Thus, they have come to complete the present invention.

That is, the present invention resides in the following items (1) to (8).

(1) A cosmetic composition containing an anionic polymer dispersant, an acid having a molecular weight of 300 or less and iron oxide particles, wherein a viscosity of the cosmetic is 15 mPa·s or less, and an average particle diameter of the iron oxide particles in the cosmetic is 100 nm or less.

(2) The cosmetic composition as described in the above item (1), wherein the anionic polymer dispersant is polysodium aspartate.

(3) The cosmetic composition as described in the above item (1), wherein the iron oxide particles are red iron oxide.

(4) The cosmetic composition as described in the above item (2), wherein the iron oxide particles are red iron oxide.

(5) The cosmetic composition as described in the above item (1), wherein the acid having a molecular weight of 300 or less is at least one organic acid selected from the group consisting of glycolic acid, lactic acid, tartronic acid, glyceric acid, hydroxylbutyric acid, 2-hydroxylbutyric acid, 3-hydroxylbutyric acid, γ-hydroxylbutyric acid, malic acid, tartaric acid, citramalic acid, citric acid, isocitric acid, leucic acid, mevalonic acid, pantoic acid, ricinoleic acid, ricinelaidic acid, cerebronic acid, quinic acid and shikimic acid.

(6) The cosmetic composition as described in the above item (2), wherein the acid having a molecular weight of 300 or less is at least one organic acid selected from the group consisting of glycolic acid, lactic acid, tartronic acid, glyceric acid, hydroxylbutyric acid, 2-hydroxylbutyric acid, 3-hydroxylbutyric acid, γ-hydroxylbutyric acid, malic acid, tartaric acid, citramalic acid, citric acid, isocitric acid, leucic acid, mevalonic acid, pantoic acid, ricinoleic acid, ricinelaidic acid, cerebronic acid, quinic acid and shikimic acid.

(7) The cosmetic composition as described in the above item (3), wherein the acid having a molecular weight of 300 or less is at least one organic acid selected from the group consisting of glycolic acid, lactic acid, tartronic acid, glyceric acid, hydroxylbutyric acid, 2-hydroxylbutyric acid, 3-hydroxylbutyric acid, γ-hydroxylbutyric acid, malic acid, tartaric acid, citramalic acid, citric acid, isocitric acid, leucic acid, mevalonic acid, pantoic acid, ricinoleic acid, ricinelaidic acid, cerebronic acid, quinic acid and shikimic acid.

(8) The cosmetic composition as described in the above item (4), wherein the acid having a molecular weight of 300 or less is at least one organic acid selected from the group consisting of glycolic acid, lactic acid, tartronic acid, glyceric acid, hydroxylbutyric acid, 2-hydroxylbutyric acid, 3-hydroxylbutyric acid, γ-hydroxylbutyric acid, malic acid, tartaric acid, citramalic acid, citric acid, isocitric acid, leucic acid, mevalonic acid, pantoic acid, ricinoleic acid, ricinelaidic acid, cerebronic acid, quinic acid and shikimic acid.

According to the present invention, provided is a cosmetic composition which does not bring about precipitation and color separation even when iron oxide particles of red iron oxide and the like are used as a coloring material for a liquid cosmetic and which is excellent in a dispersibility and an aging stability and suitable for eyeliners and the like.

According to the present invention, obtained is a cosmetic composition which is suitable for eyeliners or eyebrows and charged in a liquid cosmetic applicator.

DETAILED DESCRIPTION OF THE INVENTION

The embodiments of the present invention shall be explained below in detail.

The cosmetic composition of the present invention is characterized by containing an anionic polymer dispersant, an acid having a molecular weight of 300 or less and iron oxide particles, wherein a viscosity of the cosmetic is 15 mPa·s or less, and an average particle diameter of the iron oxide particles in the cosmetic is 100 nm or less.

The anionic polymer dispersant used in the present invention is used for enhancing a dispersibility of the iron oxide particles which are a coloring material, and it may contain at least either of one or more selected from polyaspartic acid, polyglutamic acid, styrene-acrylic acid copolymers, styrene-methacrylic acid copolymers and styrene-α-methylstyrene-acrylic acid copolymers, or one or more of salts thereof. The kind of the salts thereof includes, for example, alkali salts, such as sodium, potassium, lithium and the like, ammonium salts, and alkanolamine salts such as mono-, di- and triethanolamines, triisopropanolamine and the like.

Among the above anionic polymer dispersants, at least one (alone or two or more kinds thereof, hereinafter the same shall apply) of polyaspartic acid, polyglutamic acid, the styrene-acrylic acid copolymers, the styrene-methacrylic acid copolymers and the styrene-α-methylstyrene-acrylic acid copolymers, and the salts thereof is preferably used because of an excellent dispersion stability, and poly-sodium aspartate is particularly preferably used.

A content of the above anionic polymer dispersants is preferably 1.0 to 100% by mass based a whole amount of iron oxide particles and carbon black described later. Also, it is preferably 0.1 to 10.0% by mass, more preferably 0.2 to 5.0% by mass based a whole amount of the cosmetic composition.

If a content of the above anionic polymer dispersants is less than 0.1% by mass based a whole amount of the cosmetic composition, a dispersion stability of the iron oxide particles of red iron oxide which is a coloring material is unsatisfactory. On the other hand, if it is added in an amount exceeding 10.0% by mass, the viscosity becomes too high, and the dispersion stability is not enhanced, so that it is not economical.

The acid having a molecular weight of 300 or less used in the present invention is used for enhancing the dispersion and includes, for example, one kind selected from organic acids having a molecular weight of 300 or less, such as aliphatic hydroxy acids, aromatic hydroxy acids and derivatives thereof.

The aliphatic hydroxy acids described above include, for example, glycolic acid, lactic acid, tartronic acid, glyceric acid, hydroxylbutyric acid, 2-hydroxylbutyric acid, 3-hydroxylbutyric acid, γ-hydroxylbutyric acid, malic acid, tartaric acid, citramalic acid, citric acid, isocitric acid, leucic acid, mevalonic acid, pantoic acid, ricinoleic acid, ricinelaidic acid, cerebronic acid, quinic acid and shikimic acid.

The aromatic hydroxy acids and the derivatives thereof described above include, for example, ones selected from monohydroxybenzoic acid derivatives, salicylic acid, creosotic acid (homosalicylic acid, hydroxy(methyl)benzoic acid), vanillic acid, syringic acid, dihydroxybenzoic acid derivatives, pyrocatechuic acid, resorcylic acid, protocatechuic acid, gentisic acid, orsellinic acid, trihydroxybenzoic acid derivatives, gallic acid, phenylacetic acid derivatives, mandelic acid, benzilic acid, atrolactic acid, cinnamic acid, hydrocinnamic acid derivatives, melilotic acid, phloretic acid, coumaric acid, umbellic acid, caffeic acid, ferulic acid, sinapic acid and the like.

It include preferably one selected from glycolic acid, lactic acid, tartronic acid, glyceric acid, hydroxylbutyric acid, 2-hydroxylbutyric acid, 3-hydroxylbutyric acid, γ-hydroxylbutyric acid, malic acid, tartaric acid, citramalic acid, citric acid, isocitric acid, leucic acid, mevalonic acid, pantoic acid, ricinoleic acid, ricinelaidic acid, cerebronic acid, quinic acid and shikimic acid. It is more preferably citric acid from the viewpoint of a safety of the eyeliner.

In the present invention, acids having a molecular weight exceeding 300 tend to notably aggregate the pigment, and therefore they are not preferred.

A content of the above acids having a molecular weight of 300 or less is preferably 0.01 to 2.0% by mass, more preferably 0.1 to 1.0% by mass based a whole amount of the cosmetic composition.

If a content of the above acids having a molecular weight of 300 or less is less than 0.01% by mass, the effect described above is unsatisfactory, and on the other hand, if it is added in an amount exceeding 2.0% by mass, the pH is lowered. Accordingly, both are not preferred.

The iron oxide particles used in the present invention include fine particulate red iron oxide, black iron oxide, Prussian blue, yellow iron oxide and the like, and they can be used alone or in a mixture of two or more kinds thereof. Also, the form of the particles shall not specifically be restricted, and any forms such as a spherical from, a granular form, a rod form, an acicular form, a tabular form, an amorphous from and the like can be used.

An average particle diameter of the iron oxide particles before dispersed (in blending) which can be used is varied depending on the kind of the iron oxide particles, and in the cases of, for example, red iron oxide, black iron oxide and yellow iron oxide, the particles having an average particle diameter of 2000 nm or less, preferably 100 to 1000 nm can be used. In a case of Prussian blue, the particles having, for example, a secondary particle diameter of 50000 nm or less, preferably 100 to 30000 nm can be used.

In the present invention, among the iron oxide particles described above, red iron oxide which has a high specific gravity and which is a coloring material useful for eye cosmetics such as brown color base eyeliners is used, and the targeted effects of an excellent dispersibility and no color separation are obtained.

In the present invention (including examples), the "average particle diameter" is a value measured and calculated by a dynamic light scattering method (particle diameter analyzer FPAR-1000, manufactured by Otsuka Electronics Co., Ltd.).

A content of the above iron oxide particles is preferably 1.0 to 20% by mass, more preferably 2.0 to 15% by mass based a whole amount of the cosmetic composition.

If a content of the above iron oxide particles is less than 1.0% by mass, the color is insufficiently developed, and the covering power is short. On the other hand, if it is added in an amount exceeding 20% by mass, the viscosity becomes too high. Accordingly, both are not preferred.

The cosmetic composition of the present invention can contain, in addition to the respective components described above, water (including refined water, distilled water, ion-exchanged water, purified water, ultra pure water and the like) which is a dispersant, carbon black, a film-forming resin and the like. A content of water is a balance of the cosmetic composition after adding the components described above and optional components described later. Carbon black is used as a coloring material and can tone the cosmetic composition to a brown color by using in combination with red iron oxide of the iron oxide particles described above. The carbon black which can be used shall not specifically be restricted as long as it is carbon black used for liquid cosmetics, and various kinds of carbon blacks can be used.

A content of the above carbon black is preferably 0 to 5% by mass based a whole amount of the cosmetic composition, and when toning the cosmetic composition to a brown color by using in combination with red iron oxide of the iron oxide particles described above, it is 0.1 to 2% by mass.

The film-forming resin which can be used includes, for example, emulsion resins of copolymers prepared by two or more kinds of monomers selected from the group consisting of acrylic acid, methacrylic acid or alkyl esters or derivatives thereof, styrene and vinyl acetate.

A content of the above film-forming resin (emulsion resin) is preferably 2 to 15% by mass, more preferably 2 to 10% by mass in terms of a solid content (resin content) based a whole amount of the cosmetic composition from the viewpoints of the water-resistant performance and the coating performance.

Further, optional components used for conventional liquid cosmetics in addition to the respective essential components described above can be contained in the liquid cosmetic of the present invention. To be specific, antiseptic agents, antioxidants, neutralizing agents, UV absorbers, chelating agents, moisturizers such as 1,3-butylene glycol and the like, beauty ingredients, fragrances, viscosity modifiers, other dispersants such as polyethylene glycol alkyl ethers, and the like can be contained in suitable amounts as long as the effects of the present invention are not damaged.

A viscosity of the cosmetic composition of the present invention is controlled to 15 mPa·s or less, preferably 10 mPa·s or less and more preferably 2 to 8 mPa·s.

If the above viscosity exceeds 15 mPa·s or less, a flowing property of the composition is notably reduced, and therefore it is not preferred.

The viscosity ranges described above can be controlled by suitably combining the respective raw materials such as the kind of the iron oxide particles used and an average particle diameter thereof, the anionic polymer dispersant and the kind of the acid having a molecular weight of 300 or less, combining the respective contents in suitable ranges and employing a suitable dispersing method.

In the present invention, the above viscosity is a value measured on viscosity measuring conditions (including examples and the like described later), to be specific, obtained by measuring the resulting cosmetic composition at a standard rotor: 50 rpm (shear rate: 192 s$^{-1}$) and a temperature of 25° C. by means of an ELD type viscometer manufacture by Toki Sangyo Co. Ltd.

In the cosmetic composition of the present invention, an average particle diameter of the iron oxide particles contained in the cosmetic (after dispersed) is controlled to 100 nm or less.

If an average particle diameter of the iron oxide particles contained in the cosmetic (after dispersed) exceeds 100 nm, the particles settle down, and therefore it is not preferred. The lower the lower limit value of the average particle diameter described above, the more preferred, and it is about 30 nm from the viewpoints of the production technology and the cost.

The average particle diameter of the iron oxide particles contained in the cosmetic (after dispersed) described above can be controlled by suitably combining the respective raw materials such as the kind of the iron oxide particles used and an average particle diameter thereof, the anionic polymer dispersant and the kind of the acid having a molecular weight of 300 or less, combining the respective contents in suitable ranges and employing a suitable dispersing method.

The cosmetic composition of the present invention is prepared by dispersing the anionic polymer dispersant, the kind of the acid having a molecular weight of 300 or less, the iron oxide particles, water and the other components on suitable dispersing conditions by means of a disperser such as, for example, a homomixer, a sand mill, a supersonic homogenizer, a high pressure homogenizer and the like, whereby the average particle diameter of the iron oxide particles contained in the cosmetic (after dispersed) can be controlled to 100 nm or less.

When a (multiple) supersonic homogenizer and a high pressure homogenizer are preferably used as the disperser, the dispersing condition is set to a frequency of 20 to 30 KHz in a case of, for example, the supersonic homogenizer, and it is set to a pressure of 150 to 245 MPa in a case of the high pressure homogenizer, whereby the average particle diameter of the iron oxide particles contained in the cosmetic (after dispersed) can be controlled to 100 nm or less.

The cosmetic composition (pigment dispersion for cosmetics) obtained can be used by filling in a liquid cosmetic applicator (vessel) using a brush or a pen feed as an applying means.

The liquid cosmetic applicator which can be used shall not specifically be restricted as long as it is, for example, a liquid cosmetic applicator equipped with a brush or a pen feed for an eyeliner or an eyebrow.

It includes preferably an applicator which is equipped with an applying body such as a brush (brush pencil) and a pen feed for an eyeliner or an eyebrow, and an applying means constituted from a rubber, an elastomer or a closed cell foam having a restoring property and which is provided with a vessel filled with a liquid cosmetic.

To be specific, preferably used are the liquid cosmetic applicators which are provided respectively, as shown in FIG. 1, FIG. 2, FIG. 3A and FIG. 3B, with mechanisms of a rotary feeding type, a cosmetic charging system applicator type and a collector system applicator type and which are excellent in a usability, a convenience and a coating property.

Figure 1:
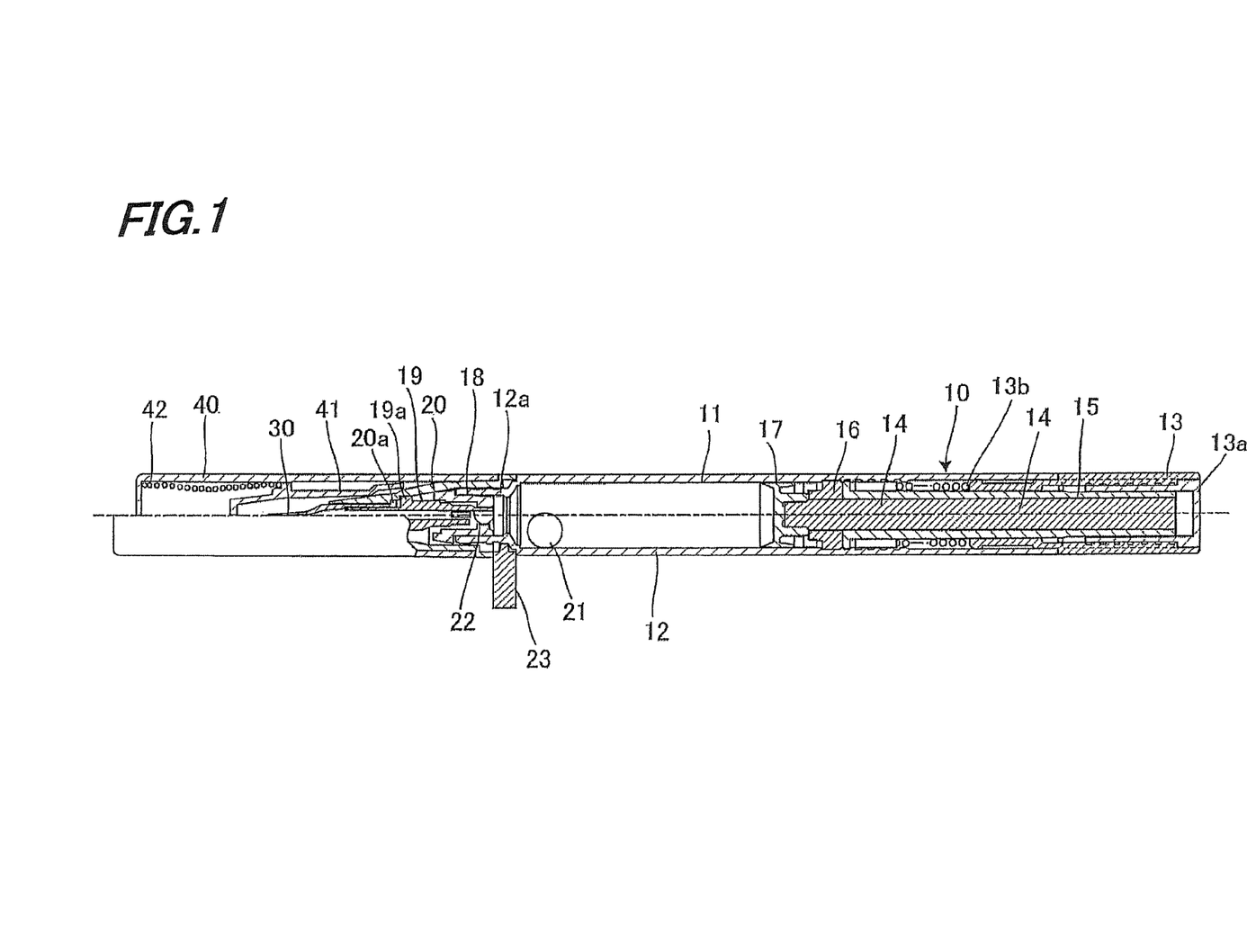
FIG. 1 is a partial cross section showing one example of the liquid cosmetic applicator charged with the cosmetic composition of the present invention. The mechanism of FIG. 1 is one example of an applicator of a rotary feeding type.

The liquid cosmetic applicator of the rotary feeding type is provided, as shown in FIG. 1, with a coating part 30 formed by a brush (brush pen) mounted in front of a cosmetic storing vessel 11 which is a storing part for the liquid cosmetic of the present invention (hereinafter referred to merely as the liquid cosmetic) stored in front of a liquid pressing mechanism 10, wherein the liquid cosmetic is discharged by the liquid pressing mechanism 10.

The liquid pressing mechanism 10 is constituted so that the liquid cosmetic in the vessel (storing part) 11 is delivered by relatively rotating a delivering member 13 arranged in a rear end part of a holder main body 12 in a peripheral direction to the holder main body 12, whereby the liquid cosmetic is supplied to the coating part 30.

The liquid pressing mechanism 10 of the above applicator is provided with the delivering member 13 rotatably interfitted with a rear end of the holder main body 12, a driving cylinder 15 conducting a rotating force of the delivering member 13 by a user to a screw rod 14, a screw body 16 which is fixed to the holder main body 12 and with which the screw rod 14 is screwed, the screw rod 14 with which a piston body 17 is rotatably engaged at a tip, and the piston body 17 which slides in an inside of the storing part 11 of the holder main body 12. It is provided with the structure that the rotation of the delivering member 13 is conducted to the screw rod 14 via the driving cylinder 15 and that the rotation of the above screw rod 14 causes the screw rod 14 and the piston body 17 to move forward via a female screw of the nut-shaped screw body 16 to deliver the liquid cosmetic from an inside of the storing part 11 to the coating part 30.

In the delivering member 13, a cylindrical operating part which is closed by inserting a crown 13a into a rear end is rotatably inserted, as shown in FIG. 1, into a rear end part of the holder main body 12, and is exposed. The driving cylinder 15 is inserted into the delivering member 13 and fixed in a rotational direction, and the screw body 16 is mounted fixably to a rotational direction and relatively rotatably to an axial direction in an inside of the driving cylinder 15. The mark 13b is a spring member and pushes backward the delivering member 13 which is a rotating body.

In the above applicator, a sealing part 18, a joint member 19, a front holder 20 and the coating part 30 are mounted at a front end part 12a of the holder main body 12 by insertion. The liquid cosmetic is received in the storing part 11 of the holder main body 12, and the liquid cosmetic delivered from the storing part 11 passes through a passage in the joint member 19 and is discharged into the coating part 30 to make it usable for coating. Also, a cap 40 is formed so that it can be mounted on the front holder 20 to cover the coating part 30 and the front holder 20 after using.

In FIG. 1, the mark 21 shows a stirring ball for stirring the liquid cosmetic in the storing part 11 by reciprocation motion, and the mark 22 shows a sealing ball. Also, the mark 41 shows an inner cap in the cap 40, and the mark 42 shows a spring for pushing backward the inner cap. The stirring ball 21 may be omitted.

Further, the mark 23 shows a stopper in which a ring-shaped part is mounted between a rear end of the front holder 20 and a front face of a step-wise site in the front end part 12a of the holder main body 12 in order to set the sealing part 18, the joint member 19, the front holder 20 and the coating part 30 in a position in which a passage of the liquid cosmetic flowing to the coating part 30 is closed in non-use time. The ring-shaped part of the above stopper 23 is partially cut off, and a holding part is integrally formed at a side opposite to the cut-off part. The ring-shaped part is expanded in a diameter from the cut-off part by pulling the holding part and can be detached from a space between a rear end of the front holder 20 and the front end part 12a of the holder main body 12.

As shown in FIG. 1, the sealing ball 22 is inserted in non-use time into an inner diameter part of the sealing part 18 which is a receiving part for the ball to tightly seal it so that the liquid cosmetic does not flow into a coating part 30 side. On the other hand, the stopper 23 is pulled out of the holder main body 12 in use time and pushed into a rear end side of the front holder 20 by the user, whereby a rear end narrow diameter part of the joint member 19 strikes against the sealing ball 22, and the sealing ball 22 is detached from the inner diameter part of the sealing part 18 and introduced into the storing part 11. The liquid cosmetic in the above storing part 11 flows into a liquid passage of the coating part 30 from an inner diameter part of the joint member 19 and is supplied from an inside thereof to the coating part 30 to make it possible to coat the liquid cosmetic on the object.

Figure 2:
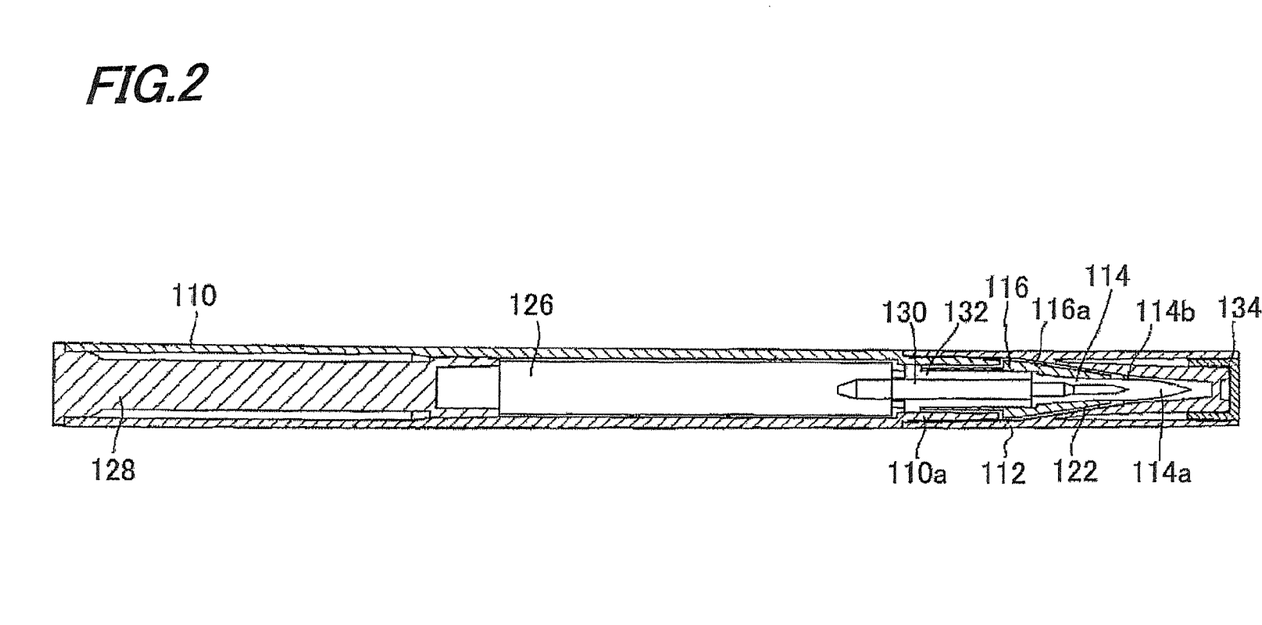
FIG. 2 is a partial cross section showing another example of the liquid cosmetic applicator charged with the cosmetic composition of the present invention. The mechanism of FIG. 2 is one example of an applicator of a cosmetic charging type.

The liquid cosmetic applicator of the cosmetic charging system applicator type is a cosmetic charging system applicator having a structure in which provided are, as shown in FIG. 2, a shaft 110 charged with a cosmetic impregnated in a sliver 126, a coating part 114 provided at a tip part 110a of the shaft and used for coating the cosmetic on an object, and a holding member 116 covering an outer periphery at a shaft 110 side (base side) of the coating part 114 excluding a tip part 114a of the coating part 114 to feed the cosmetic contained in an inside of the shaft 110 to the coating part 114, wherein a cap 112 which is detachably constituted is provided at the tip part 110a of the shaft in order to cover the coating part 114 and the holding member 116.

The coating part 114 is sharpened at the tip part 114a. Also, the coating part 114 has a form of a brush prepared by bundling fibers. To be specific, the coating part 114 is formed by arranging (sharpening) plural resin-made fiber bundles (specific example: the material of the fibers is made of polybutylene terephthalate (PBT), a fiber thickness is 0.1 to 0.14 mm) in a brush form so that the tip part 114a is tapered, integrating the rear end part by heating and welding, and expanding a diameter thereof in a flange form. In addition to the above, the coating part 114 may be formed by putting fibers together.

In the cosmetic charging system applicator in the above embodiment, the sliver 126 of an ink reservoir is received therein from an central part of the shaft 110 to the tip part 110*a*, and the sliver 126 is sealed and supported by a plug 128 inserted from a rear end of the shaft 110.

An ink feed 130 comprising an open-cell foam is arranged at an aperture of the tip part 110*a* of the shaft. An end of this feed 130 is inserted into a tip part of the sliver 126, and on the other hand, a tip thereof is inserted into an end part of the coating part 114 to induce an ink absorbed in the sliver 126 to the coating part 114. Also, the feed 130 is installed via an approximately cylindrical supporter 132 in the shaft tip part 110*a* which is reduced a little more by a step in a diameter than the main body (reduced more by a thickness of the cap 112 in a diameter), and a cylindrical rear end part of the holding member 116 is inserted into a space between an outer periphery of the supporter 132 and an inner periphery of the shaft tip part 110*a*.

A tip part of the holding member 116 is positioned in front of the shaft tip part 110*a* to cover an outer peripheral surface 114*b* of the coating part 114, and an outer peripheral surface 116*a* of the holding member is pointed gradually in a conical side form or a taper form.

Figure 3A:
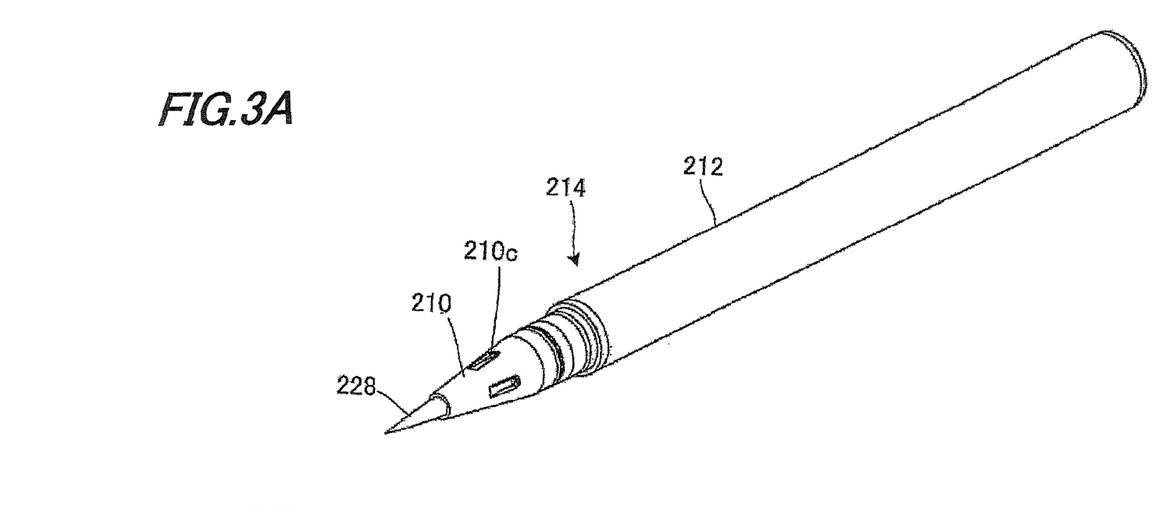
FIG. 3A is a perspective drawing showing still another example of the liquid cosmetic applicator charged with the cosmetic composition of the present invention.
Figure 3B:
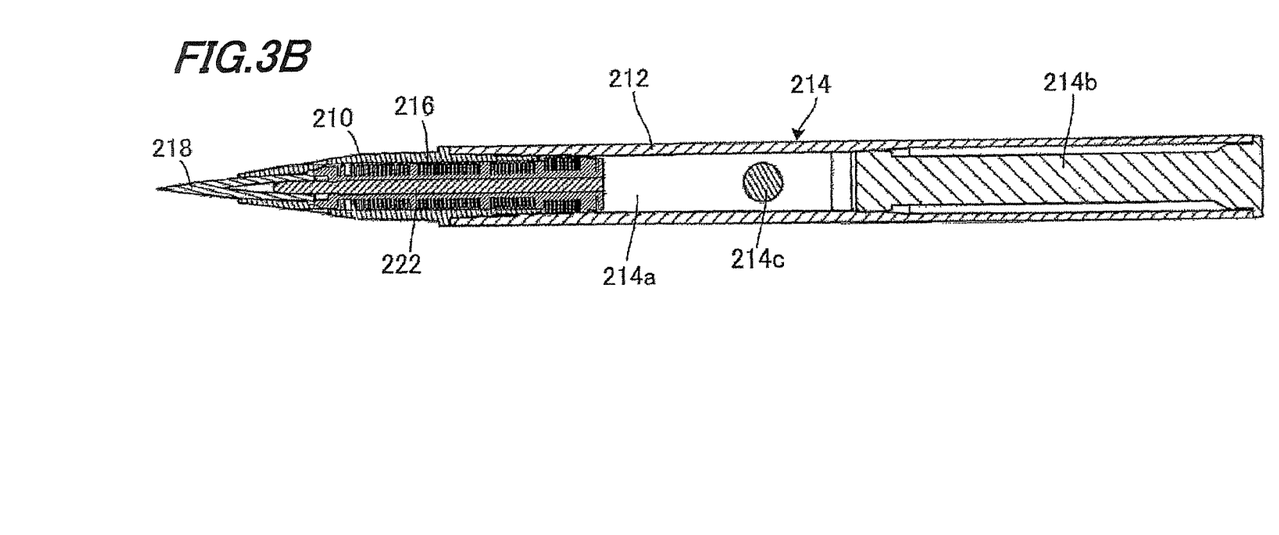
FIG. 3B is a partial cross section of the same liquid cosmetic applicator as shown in FIG. 3A. The mechanism of the liquid cosmetic applicator of FIGS. 3A and 3B is one example of an applicator of a collector type.

In the liquid cosmetic applicator of the collector system applicator type, provided is, as shown in FIG. 3A, a shaft body 214 in which a front shaft 210 is engaged with a shaft main body 212 at a rear side of the front shaft 210, and arranged is, as shown in FIG. 3B, a pectinated collector 216 of an embodiment in which plural single wafer parts are disposed to a shaft direction in front of the shaft body 214, wherein a coating liquid is received in a receiving space 214*a* at a rear part of the shaft body 214.

The shaft main body 212 at a rear part of the shaft body 214 described above is formed in a pipe form which is communicated in an inside and which is opened at front and rear sides. A plug 214*b* is inserted into a rear part of the shaft main body 212 which is a rear part of the shaft body described above to close the rear part of the shaft main body 212, and a space (also a space in an inside of the shaft main body 212 of the shaft main body 212) in an inside of the shaft body 214 interposed by a front end of the above plug 214*b* and a rear end of the collector 216 is the receiving space 214*a*.

An impregnant matter such as a sliver and the like is not disposed the above receiving space 214*a*, and a coating liquid is received directly therein, and a stirring matter (a ball and the like) 214*c* for stirring the above coating liquid is disposed therein.

The front shaft 210, the shaft main body 212, the collector 216, the cap and the like can be formed as resin moldings. Also, ball matters made of metals, resins and the like can be used for the stirring matter 214*c*.

The collector 216 is of a structure in which it is covered with and held by the front shaft 210 and the shaft main body 212.

A writing part 218 comprising a brush body which is pointed gradually in a taper form is protruded from an aperture at a tip part of the front shaft 210, and the cap covering the writing part 218 is of a structure in which it is detachably engaged with the front shaft 210 described above. The front shaft 210 assumes an almost conical side form and is formed so that it is pointed gradually, and a front angle of the above front shaft 210 is set to almost the same angle as a front angle of the writing part 218.

The writing part 218 is a tapered brush body comprising resin fibers, a natural fiber bundle or a resin-made porous matter. A diameter of the writing part 218 is expanded in a flange form at a rear end part, and a part in which the diameter is expanded is engaged with an inside of the front shaft 210 so that it is prevented from coming out therefrom.

The writing part 218 is suitably a brush body, and in addition thereto, various coating bodies for coating liquids can be used therefor.

A cup-like inner cap is back and forward movably disposed in an inside of the cap in order to enhance an air tightness of the writing part 218, and a spring for pushing the above inner cap backward is arranged.

The bellows-like collector 216 is disposed at a rear of the writing part 218 in an inside of the front shaft 210 which is hollow and formed in a taper form, and an inner feed 222 is arranged in a hollow part of the collector 216 so that it passes therethrough. The inner feed 222 can be constituted from a capillary member such as a resin fiber bundle, a natural fiber bundle, a resin-made porous matter and the like.

The inner feed 222 is not protruded into the receiving space 214*a* of the shaft body 214 from a rear end part of the collector 216 (refer to FIG. 3B). A rear end part of the inner feed 222 almost agrees with a rear end surface of the collector 216. A rear end of the inner feed 222 is not protruded into the receiving space 214*a* by allowing the inner feed 222 to agree with the collector 216, and a volume in the receiving space 214*a* can be secured. Also, a rear end of the inner feed 222 is not protruded into the receiving space 214*a*, and therefore when the stirring matter 214*c* is provided in the receiving space 214*a*, it does not strike against the inner feed 222 to deform it if the stirring matter 214*c* moves in the receiving space 214*a*, so that the coating liquid can sufficiently be penetrated.

In the liquid cosmetic applicators of the forms described above, the cosmetic composition has been explained by referring to liquid cosmetic applicators for liquid eyeliners and liquid eyeshadows which are the cosmetic compositions corresponding to the liquid cosmetics of the present invention, but it shall not be restricted to them and can be applied as well to eyebrow applicators for drawing lines on eyebrows and applicators for drawing lines on skins.

The liquid cosmetic applicator of the rotary feeding type shown in FIG. 1 has been used as a liquid pressing mechanism for the liquid cosmetic applicator of the form described above, but a liquid cosmetic applicator of a knock feeding type may be used.

In the cosmetic composition of the present invention thus constituted, even when the iron oxide particles of red iron oxide and the like having a high specific gravity are used as the coloring material for the liquid cosmetic, an average particle diameter of the iron oxide particles contained in the liquid cosmetic (after dispersed) can be kept as very small as 100 nm or less for a long period by containing the anionic polymer dispersant, the acid having a molecular weight of 300 or less and the iron oxide particles, suitably combining the respective raw materials such as the kind of the iron oxide particles used, the anionic polymer dispersant and the kind of the acid having a molecular weight of 300 or less, combining the respective contents in suitable ranges, and employing the suitable dispersing method. Accordingly, obtained is the cosmetic composition which does not cause precipitation by aggregation and does not bring about color separation and which is excellent in a dispersibility and an aging stability. Thus, even when the cosmetic composition of the present invention is stored for a long period of time in a vessel such as a liquid cosmetic applicator used, a difference in the concentration is not produced at upper and lower parts in the vessel, and a dispersibility and an aging stability thereof are maintained over a long period of time, so that obtained is the cosmetic composition which is less liable to bring about color separation at a tip and the like of the brush in the applicator vessel of an eyeliner using the brush 30 as shown in FIG. 1 described above and which is suitable for a liquid cosmetic such as eyeliner liquids and the like.

EXAMPLES

Next, the present invention shall be explained in further details with reference to examples and comparative examples, but the present invention shall not be restricted by the examples and the like shown below.

Examples 1 to 6 and Comparative Examples 1 to 4

Cosmetic compositions (blend unit: % by mass, whole amount: 100% by mass) which were aqueous liquid cosmetics having blend compositions shown in the following Table 1 were prepared by the following method to measure the viscosity values of the respective liquid cosmetics and the average particle diameters of the iron oxide particles in the respective liquid cosmetics after dispersed by the measuring methods described above and evaluate the upper and lower concentration difference in the vessel, the separation of the cosmetics and the followability by the following evaluating methods.

The results thereof are shown in the following Table 1.
Preparing Methods of Cosmetic Compositions The cosmetic compositions which were the aqueous liquid cosmetics having the blend compositions shown in the following Table 1 were prepared by the method which has so far been used, that is, adding the iron oxide particles of the coloring material and the dispersant to water which is a vehicle, dispersing them by means of a supersonic homogenizer US-150E (manufactured by NIHONSEIKI KAISHA LTD., output: 1200 W, tip of an oscillation element: ϕ50), then adding the other components and mixing them.

Evaluating Method of Upper and Lower Concentration Difference

The direct liquid type eyeliner shown in FIG. 1 was charged with the cosmetic composition, and an applying body thereof was held in upward and downward postures to evaluate an upper and lower concentration difference based on the following evaluation criteria by observing the situations of the drawn lines after one month passed at room temperature.
Evaluation Criteria:
○: no upper and lower concentration difference
Δ: upper and lower concentration difference is present without change in hue
x: not only upper and lower concentration difference but also hue are clearly observed
Evaluating Method of Cosmetic Separation A glass sealed vessel was charged with the cosmetic composition, and the situations of the drawn lines after one month passed at room temperature were observed visually to evaluate them based on the following evaluation criteria.
Evaluation Criteria:
○: no separation is observed
Δ: part of supernatant is slightly observed
x: separation is caused, and the coloring material is observed to settle down
Evaluating Method of Followability The liquid cosmetic applicator shown in FIG. 1 was charged with the cosmetic composition, and a flowing situation of the cosmetic when the applicator was used was evaluated based on the following evaluation criteria.
Evaluation Criteria:
○: the cosmetic can smoothly be coated
Δ: the cosmetic is disconnected in certain parts
x: the cosmetic is not delivered at all

TABLE 1

|  | Example | | | | | | Comparative Example | | | |
| --- | --- | --- | --- | --- | --- | --- | --- | --- | --- | --- |
|  | 1 | 2 | 3 | 4 | 5 | 6 | 1 | 2 | 3 | 4 |
| Poly-sodium aspartate | 3.9 | 2.1 | 4 | 0.6 | 3.9 | 0.8 | 1.2 | 1.2 | 1.2 | 0.6 |
| Red iron oxide (average particle diameter before dispersed: 500 nm) | 9 | 5 | 13 | 4 | 9 | 4 | 12 | 12 | 12 | 4 |
| Black iron oxide (average particle diameter before dispersed: 100 to 200 nm) |  |  |  |  | 1.2 | 4 | 8.8 | 8.8 | 8.8 |  |
| Prussian blue (secondary particle diameter before dispersed: 30 μm or less) |  |  |  |  |  |  | 2.4 | 2.4 | 2.4 |  |
| Carbon black | 1.2 | 1 | 1.5 | 1 |  |  |  |  |  | 1 |
| Citric acid | 0.5 | 0.3 | 0.3 | 0.3 | 0.6 | 0.2 |  |  |  |  |
| Polyethylene glycol behenyl ether *1 | 0.3 | 0.2 | 0.4 | 0.2 | 0.3 | 0.2 |  |  |  | 0.2 |
| Polyethylene glycol lauryl ether *2 |  |  |  |  |  |  | 2 | 2 | 2 |  |
| Acrylic acid ester copolymer emulsion *3 | 20 | 20 | 20 | 20 | 20 | 20 | 9 | 20 | 30 | 20 |
| 1,3-Butylene glycol | 9 | 8 | 8 | 8 | 8 | 10 | 4 | 4 | 4 | 8 |
| 2-Amino-2-methyl-1-propanol |  |  |  |  |  |  | 0.2 | 0.2 | 0.2 |  |
| Antiseptic agent *4 | 0.8 | 0.8 | 0.8 | 0.8 | 0.8 | 0.8 | 0.8 | 0.8 | 0.8 | 0.8 |
| Refined water | Balance | Balance | Balance | Balance | Balance | Balance | Balance | Balance | Balance | Balance |
| Viscosity (mPa · s) 192 s$^{-1}$ | 4 | 3 | 5 | 3 | 4 | 4 | 8 | 12 | 16 | 3 |
| Average particle diameter (nm) of iron oxide particle after dispersed | 30 | 40 | 60 | 30 | 30 | 40 | 200 | 200 | 200 | 140 |
| Upper and lower concentration difference | ○ | ○ | ○ | ○ | ○ | ○ | X | X | X | Δ |

TABLE 1-continued

|  | Example | | | | | | Comparative Example | | | |
| --- | --- | --- | --- | --- | --- | --- | --- | --- | --- | --- |
|  | 1 | 2 | 3 | 4 | 5 | 6 | 1 | 2 | 3 | 4 |
| Cosmetic separation | ◯ | ◯ | ◯ | ◯ | ◯ | ◯ | X | X | X | X |
| Followability | ◯ | ◯ | ◯ | ◯ | ◯ | ◯ | ◯ | Δ | X | ◯ |

*1 to *4 in Table 1 show the following.
*1: NIKKOL BB-30 (manufactured by Nikko Chemicals Co., Ltd.)
*2: NIKKOL BL-21 (manufactured by Nikko Chemicals Co., Ltd.)
*3: copolymer emulsion comprising two or more components of acrylic acid, methacrylic acid and (C1 to C4 and C8) alkyl esters thereof solid content: 45% by mass
*4: mixture of methylparaben, ethylparaben, ethylparaben and phenoxyethanol As apparent from the results shown in Table 1 described above, it has become clear that since the cosmetic compositions prepared in Examples 1 to 6 falling in the scope of the present invention do not cause an upper and lower concentration difference and are excellent in an aging dispersion stability as compared with the cosmetic compositions prepared in Comparative Examples 1 to 4 falling outside the scope of the present invention, so that they are cosmetic compositions which are not required to be stirred in charging into vessels and which do not require as well a stirring work before the users use them.

To observe the comparative examples, the composition in Comparative Example 1 was close to that in Example 3 of JP-A 2003-231614 from which a chelating agent and the like were removed, wherein the acid having a molecular weight of 300 or less was not contained; an average particle diameter of iron oxide particles in the cosmetic (after dispersed) was 200 nm; and the result was that the concentration difference and the hue difference were clearly observed after aged in a glass sealed vessel which was different from a brush pen type vessel. In Comparative Example 2, the acrylic acid ester copolymer emulsion was increased more in an amount than in Comparative Example 1 described above to elevate a viscosity of the vehicle, whereby it was tried to inhibit the iron oxide particles from settling down, but it resulted only in the deterioration of the followability, and the concentration difference and the hue difference were not improved after the passage of time. Further, in Comparative Example 3, the acrylic acid ester copolymer emulsion was increased further more in an amount to set the viscosity to 16 mPa·s which falls outside the range of the present invention, but the result was further worsened. In Comparative Example 4, citric acid which is the acid having a molecular weight of 300 or less for enhancing the dispersibility was removed from the composition in Example 4 described above, and the composition thus obtained fell outside the range of the present invention; an average particle diameter of red iron oxide in the cosmetic (after dispersed) was 140 nm; and the cosmetic was observed to be separated in the glass sealed vessel.

What is claimed is:

1. A cosmetic composition containing an anionic polymer dispersant selected from Group A below, an organic acid having a molecular weight of 300 or less selected from Group B below and only one or two kinds of the iron oxide particles selected from Group C below and not containing other iron oxide particles, wherein a viscosity of the cosmetic is 15 mPa·s or less at 25° C., and an average particle diameter of the iron oxide particles in the cosmetic is 100 nm or less;

Group A: polyaspartic acid, polyglutamic acid, styrene-acrylic acid copolymers, styrene-methacrylic acid copolymers and styrene-α-methylstyrene-acrylic acid copolymers, and salts thereof;

Group B: aliphatic hydroxy acids and aromatic hydroxy acids; and

Group C: red iron oxide, black iron oxide, and yellow iron oxide.

2. The cosmetic composition as described in claim 1, wherein the anionic polymer dispersant is poly-sodium aspartate.

3. The cosmetic composition as described in claim 2, wherein the iron oxide particles contain red iron oxide.

4. The cosmetic composition as described in claim 2, further containing carbon black.

5. The cosmetic composition as described in claim 2, further containing a film-forming resin.

6. The cosmetic composition as described in claim 1, wherein the iron oxide particles contain red iron oxide.

7. The cosmetic composition as described in claim 1, further containing carbon black.

8. The cosmetic composition as described in claim 1, further containing a film-forming resin.

* * * * *